(12) United States Patent
Liu et al.

(10) Patent No.: US 7,808,691 B2
(45) Date of Patent: *Oct. 5, 2010

(54) GREEN ELECTROCHROMIC MATERIALS

(75) Inventors: Lu Liu, Seattle, WA (US); Chunye Xu, Seattle, WA (US); Minoru Taya, Mercer Island, WA (US)

(73) Assignee: University of Washington, Seattle, WA (US)

(*) Notice: Subject to any disclaimer, the term of this patent is extended or adjusted under 35 U.S.C. 154(b) by 286 days.

This patent is subject to a terminal disclaimer.

(21) Appl. No.: 11/876,513

(22) Filed: Oct. 22, 2007

(65) Prior Publication Data

US 2009/0067030 A1 Mar. 12, 2009

Related U.S. Application Data

(60) Continuation-in-part of application No. 11/774,438, filed on Jul. 6, 2007, now Pat. No. 7,505,191, and a continuation-in-part of application No. 11/223,794, filed on Sep. 9, 2005, now Pat. No. 7,298,541, and a continuation-in-part of application No. 11/070,392, filed on Mar. 1, 2005, now Pat. No. 7,256,923, and a continuation-in-part of application No. 10/917,954, filed on Aug. 13, 2004, now Pat. No. 7,450,290, and a continuation-in-part of application No. 10/755,433, filed on Jan. 12, 2004, now Pat. No. 7,002,722, which is a division of application No. 10/180,222, filed on Jun. 25, 2002, now Pat. No. 6,747,780.

(60) Provisional application No. 60/608,438, filed on Sep. 9, 2004, provisional application No. 60/549,035, filed on Mar. 1, 2004, provisional application No. 60/495,310, filed on Aug. 14, 2003, provisional application No. 60/523,007, filed on Nov. 18, 2003.

(51) Int. Cl.
*G02F 1/15* (2006.01)

(52) U.S. Cl. ............... 359/265; 359/267; 549/29; 549/50; 548/453

(58) Field of Classification Search ............ 359/265
See application file for complete search history.

(56) References Cited

U.S. PATENT DOCUMENTS

| 4,702,963 A | 10/1987 | Phillips et al. ............ 428/426 |
| 4,761,061 A | 8/1988 | Nishiyama et al. ......... 359/265 |
| 4,768,865 A | 9/1988 | Greenberg et al. ......... 359/266 |

(Continued)

FOREIGN PATENT DOCUMENTS

JP 62265630 11/1987

OTHER PUBLICATIONS

Sapp, Shawn A. et al. 1998, "High Contrast Ratio and Fast-Switching Dual Polymer Electrochromic Devices." *Chem. Mater.* 10: 2101-2108.

(Continued)

*Primary Examiner*—Jessica T Stultz
(74) *Attorney, Agent, or Firm*—Ronald M. Anderson

(57) ABSTRACT

Green electrochromic (EC) materials based on thiophene, and a green EC material based on pyrazine are disclosed. A first thiophene derivative (2,3-Di-thiophen-2-yl-thieno[3,4-b]pyrazine), which was previously investigated as a nonlinear optical material, is here disclosed for its use as an EC material and for its incorporation into an EC device. Synthesis of two new thiophene derivatives (2,5-di(thien-2-yl)-3,4-di(2,2,2-trifluoro-ethoxy)-thiophene and 2,5-(2,3-dihydro-thieno[3,4-b][1,4]dioxin-5-yl)-3,4-di(2,2,2-trifluoro-ethoxy)-thiophene), and a new pyrazine derivative (2,3-dibenzyl-5,7-di(thien-2-yl)thieno[3,4-b]pyrazine) are also disclosed, since these materials are all able to selectively change state to appear a green color and can be polymerized to achieve a green EC polymer.

1 Claim, 9 Drawing Sheets

COMPOUND 1: RED STATE
COMPOUND 3: PURPLE STATE
COMPOUNDS 13/14: TRANSPARENT STATE

GREEN COLORED STATE

U.S. PATENT DOCUMENTS

| | | | |
|---|---|---|---|
| 4,786,715 A * | 11/1988 | Ishikawa et al. | 528/422 |
| 4,933,106 A | 6/1990 | Sakai et al. | 252/500 |
| 4,993,810 A | 2/1991 | Demiryont | 359/265 |
| 5,006,633 A | 4/1991 | Shikatani et al. | 528/230 |
| 5,015,086 A | 5/1991 | Okaue et al. | 351/44 |
| 5,042,923 A | 8/1991 | Wolf et al. | 359/275 |
| 5,124,833 A | 6/1992 | Barton et al. | 359/269 |
| 5,187,034 A | 2/1993 | Otagawa et al. | 429/213 |
| 5,321,544 A | 6/1994 | Parkhe et al. | 359/273 |
| 5,377,037 A | 12/1994 | Branz et al. | 359/265 |
| 5,404,244 A | 4/1995 | Van Dine et al. | 359/270 |
| 5,457,564 A | 10/1995 | Leventis et al. | 359/271 |
| 5,598,293 A | 1/1997 | Green | 359/275 |
| 5,699,192 A | 12/1997 | Van Dine et al. | 359/269 |
| 5,724,176 A | 3/1998 | Nishikitani et al. | 359/271 |
| 5,818,636 A | 10/1998 | Leventis et al. | 359/273 |
| 5,883,220 A | 3/1999 | Armand et al. | 528/322 |
| 5,888,431 A | 3/1999 | Tonar et al. | 252/583 |
| 5,905,590 A | 5/1999 | Van Der Sluis et al. | 359/275 |
| 6,005,705 A | 12/1999 | Schmidt et al. | 359/265 |
| 6,011,642 A | 1/2000 | Vink et al. | 359/273 |
| 6,136,161 A | 10/2000 | Yu et al. | 204/192.29 |
| 6,197,923 B1 | 3/2001 | Yamamoto | 528/424 |
| 6,373,618 B1 | 4/2002 | Agrawal et al. | 359/265 |
| 6,555,945 B1 | 4/2003 | Baughman et al. | 310/300 |
| 6,589,383 B1 | 7/2003 | Takaoka et al. | 156/313 |
| 6,617,462 B1 | 9/2003 | Tan et al. | 549/29 |
| 6,667,825 B2 | 12/2003 | Lu et al. | 359/265 |
| 6,728,022 B2 | 4/2004 | Asano et al. | 359/265 |
| 6,730,212 B1 | 5/2004 | Yamagishi et al. | 205/777.5 |
| 6,734,956 B2 | 5/2004 | Byrne et al. | 356/128 |
| 6,791,738 B2 | 9/2004 | Reynolds et al. | 359/265 |
| 6,806,989 B2 | 10/2004 | Berneth | 359/265 |
| 6,828,062 B2 | 12/2004 | Lu et al. | 429/213 |
| 6,855,431 B2 | 2/2005 | Varaprasad et al. | 428/432 |
| 6,906,842 B2 | 6/2005 | Agrawal et al. | 359/265 |
| 6,950,220 B2 | 9/2005 | Abramson et al. | 359/265 |
| 7,298,541 B2 * | 11/2007 | Liu et al. | 359/265 |
| 7,333,257 B2 | 2/2008 | Reynolds et al. | 359/265 |
| 2003/0072071 A1 | 4/2003 | Asano et al. | 359/265 |
| 2003/0174377 A1 | 9/2003 | Reynolds et al. | 359/265 |
| 2005/0025980 A1 | 2/2005 | Agrawal et al. | 428/426 |
| 2005/0237485 A1 | 10/2005 | Blum et al. | 351/168 |
| 2006/0066933 A1 | 3/2006 | Jagt et al. | 359/265 |
| 2007/0292606 A1 | 12/2007 | Demiryont et al. | 427/126.5 |
| 2008/0203910 A1 | 8/2008 | Reynolds | 313/506 |

OTHER PUBLICATIONS

Schwenderman, Irina et al. 2001. "Combined Visible and Infrared Electrochromism Using Dual Polymer Devices." *Advances Materials* 13:9 634-637.

Welsh, Dean M. et al. 1999. "Enhanced Contrast Ratios and Rapid Switching in Electrochromics Based on Poly (3,4-propylenediozythiophene) Derivatives." *Advanced Materials* 11:16 1379-1382.

\* cited by examiner

NEUTRAL/ YELLOW

RADICAL ION/ DARK GREEN

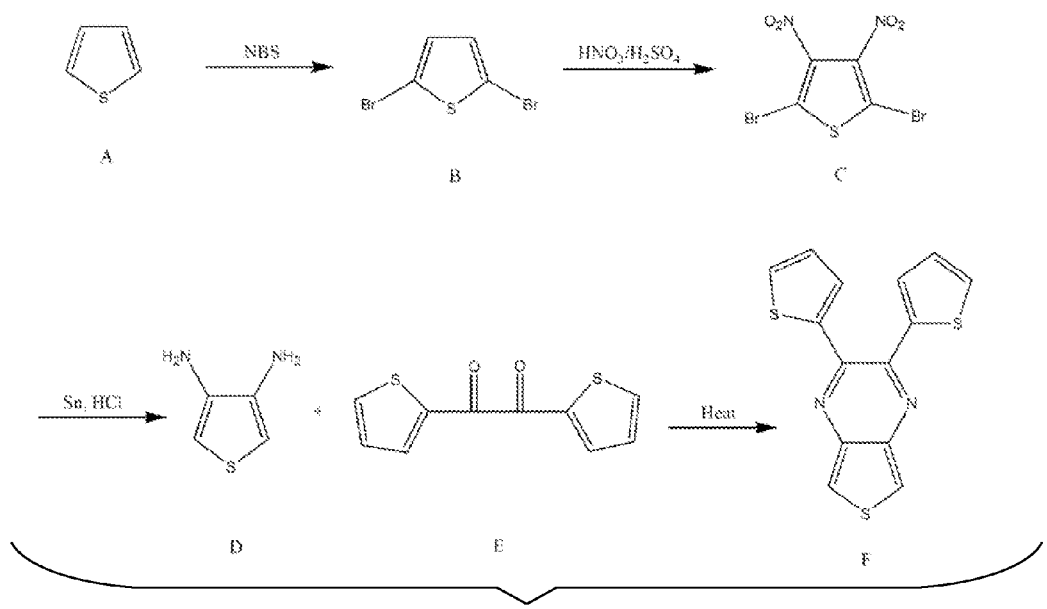
FIG. 3
PRIOR ART
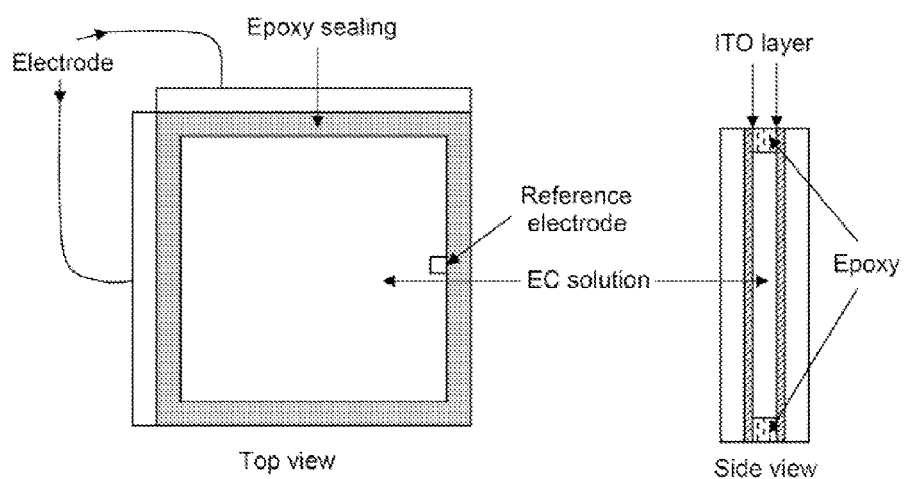
FIG. 4A  FIG. 4B

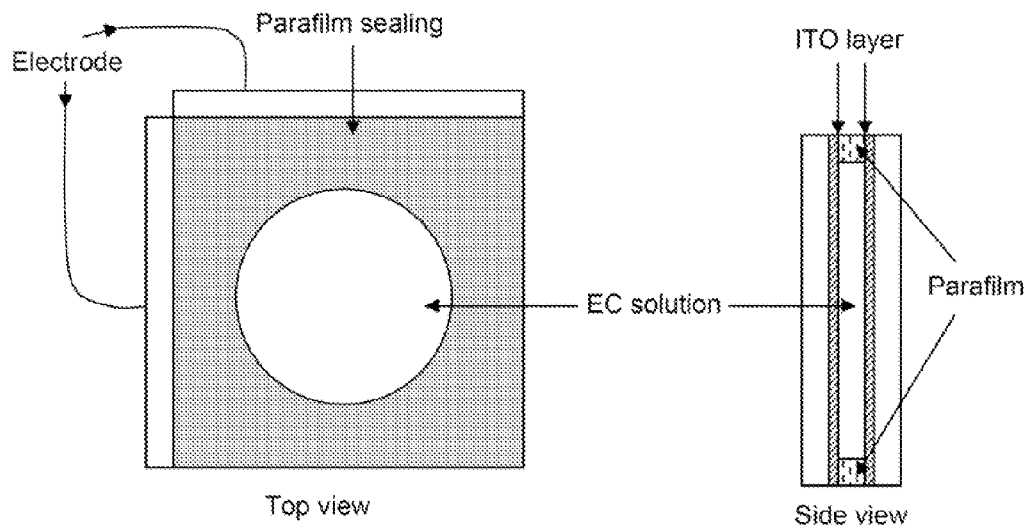
*FIG. 5A*     *FIG. 5B*
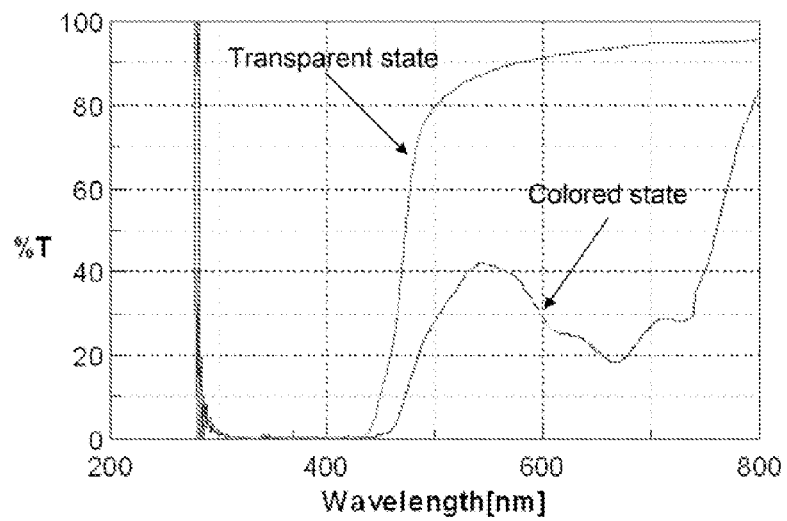
*FIG. 5C*
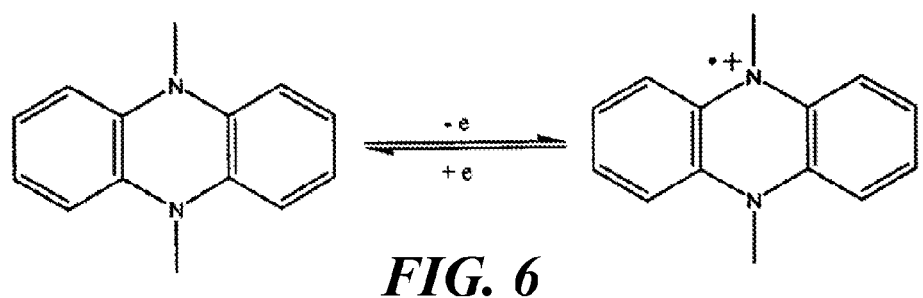
*FIG. 6*

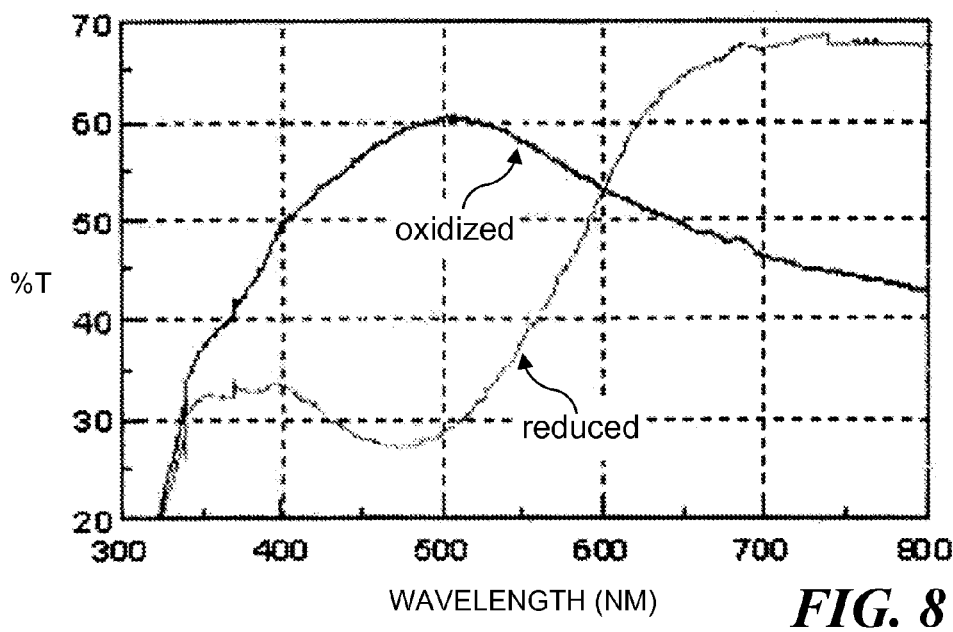
FIG. 8
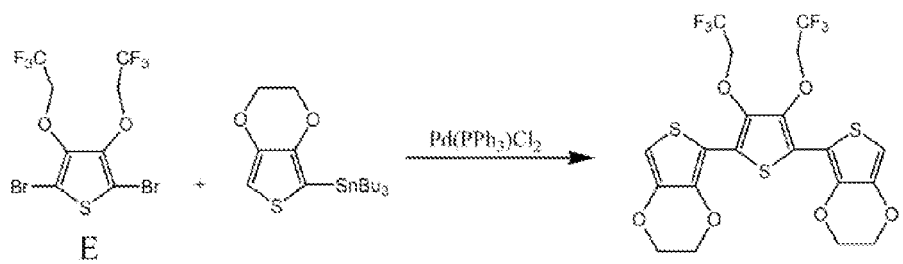
FIG. 10A          Compound 3
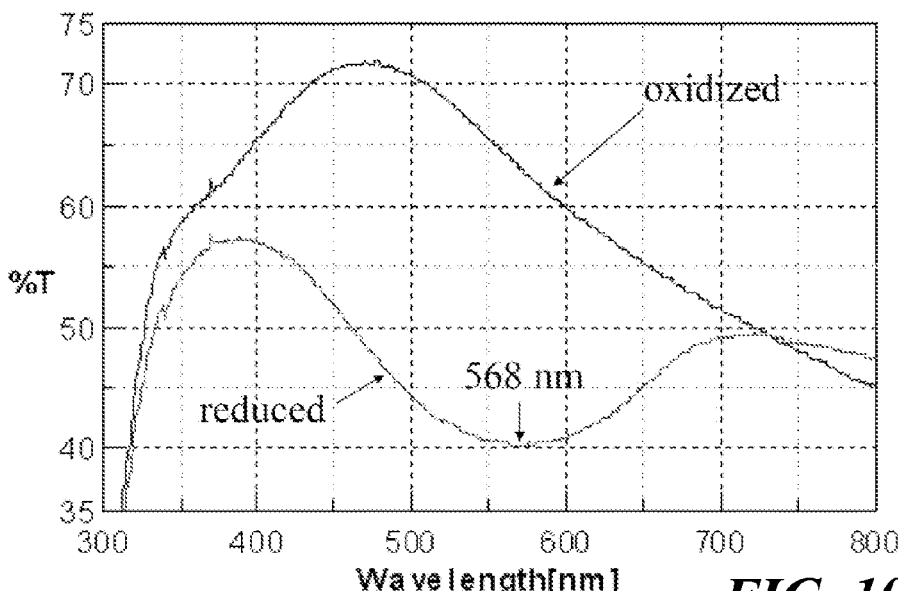
FIG. 10B

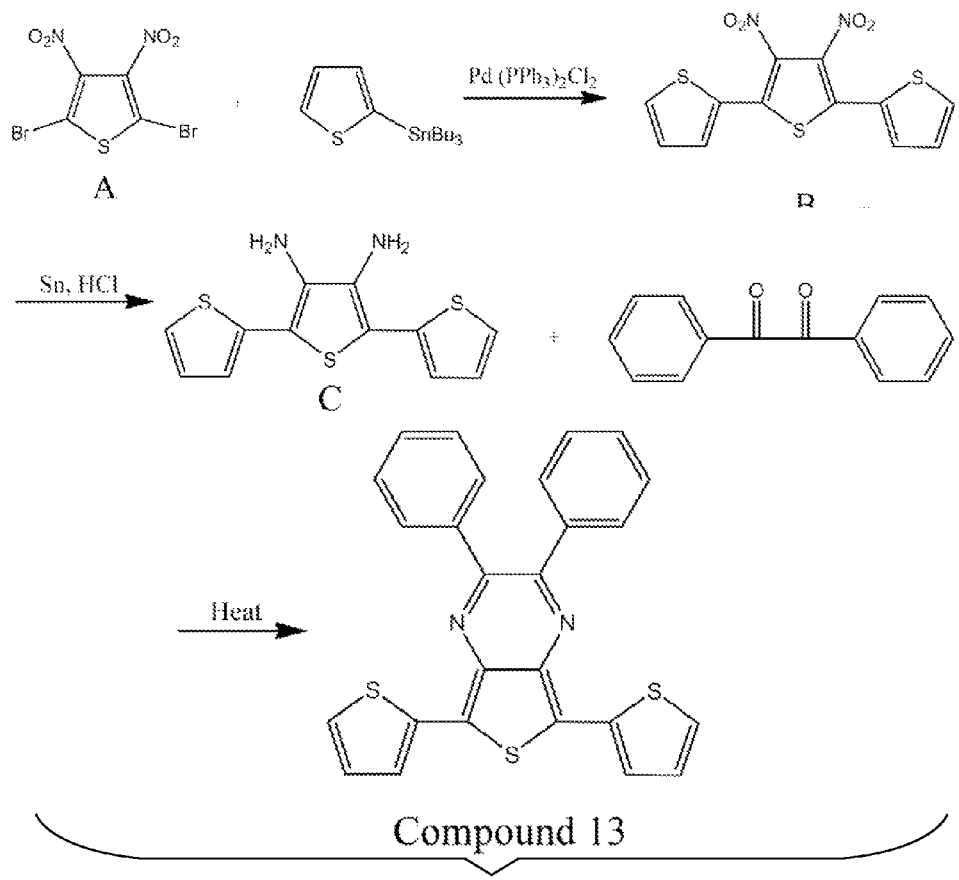
FIG. 12
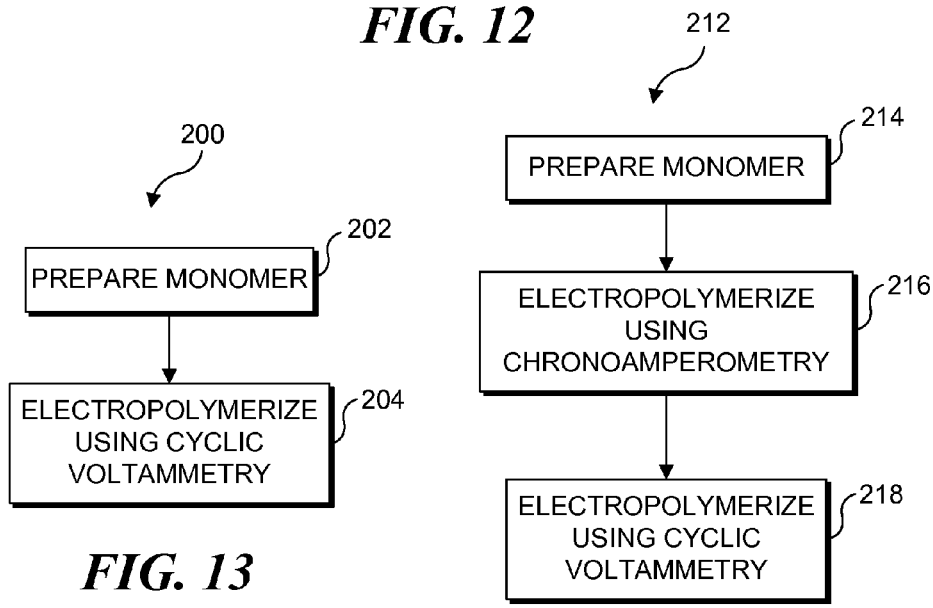
FIG. 13
FIG. 14

COMPOUND 1: RED STATE
COMPOUND 3: PURPLE STATE
COMPOUNDS 13/14: TRANSPARENT STATE

*GREEN COLORED STATE*

GREEN ELECTROCHROMIC MATERIALS

RELATED APPLICATIONS

This application is a continuation-in-part of patent applications, Ser. No. 11/774,438, filed Jul. 6, 2007, now U.S. Pat. No. 7,505,191, and Ser. No. 11/223,794, filed on Sep. 9, 2005, now U.S. Pat. No. 7,298,541. Patent application Ser. No. 11/223,794 is based on a prior copending provisional application, Ser. No. 60/608,438, filed on Sep. 9, 2004. In addition, patent application Ser. No. 11/223,794 is also a continuation-in-part of a patent application, Ser. No. 11/070,392, filed on Mar. 1, 2005, now U.S. Pat. No. 7,256,923, which itself is based on a prior copending provisional application, Ser. No. 60/549,035, filed on Mar. 1, 2004, the benefit of the filing dates of which is hereby claimed under 35 U.S.C. §§119(e) and 120. Patent application Ser. No. 11/070,392 is also a continuation-in-part of a patent application, Ser. No. 10/917,954, filed on Aug. 13, 2004, now U.S. Pat. No. 7,450,290, which itself is based on two prior copending provisional applications, Ser. No. 60/495,310, filed on Aug. 14, 2003, and Ser. No. 60/523,007, filed on Nov. 18, 2003, the benefit of the filing dates of which is hereby claimed under 35 U.S.C. §119(e) and 120. Copending patent application Ser. No. 10/917,954 is also a continuation-in-part of a patent application Ser. No. 10/755,433, filed Jan. 12, 2004, now U.S. Pat. No. 7,002,722, which in turn is a divisional of an earlier patent application, Ser. No. 10/180,222, filed Jun. 25, 2002, now U.S. Pat. No. 6,747,780, the benefit of the filing dates of which is hereby claimed under 35 U.S.C. §§119(e) and 120.1.

BACKGROUND

Electrochromic (EC) materials are a subset of the family of chromogenic materials, which includes photochromic materials, and thermochromic materials. These materials change their tinting level or opacity when exposed to light photochromic), heat (thermochromic), or an electric potential (electrochromic). Chromogenic materials have attracted widespread interest in applications relating to the transmission of light.

An early application for the use of chromogenic materials was in sunglasses or prescription eyeglasses that darken when exposed to the sun. Such photochromic materials were first developed by researchers at Corning Incorporated in the late 1960s. Since that time, it has been recognized that chromogenic materials could potentially be used to produce window glass that can vary the amount of light transmitted, although the use of such materials is clearly not limited to that prospective application. Indeed, EC technology is already employed in the displays of digital watches.

Several different distinct types of EC materials are known. Three primary types are: inorganic thin films, organic polymer films, and organic solutions. For many applications, the use of a liquid material is inconvenient, and as a result, inorganic thin films and organic polymer films appear to have more industrial applications.

For inorganic thin film-based EC devices, the EC layer is typically tungsten oxide ($WO_3$). U.S. Pat. Nos. 5,598,293; 6,005,705; and 6,136,161 describe an inorganic thin film EC device based on a tungsten oxide EC layer. Other inorganic EC materials, such as molybdenum oxide, are also known. While many inorganic materials have been used as EC materials, difficulties in processing and a slow response time associated with many inorganic EC materials have created the need for different types of EC materials.

Conjugated, redox-active polymers represent one different type of EC material. These polymers (cathodic or anodic polymers) are inherently electrochromic and can be switched electrochemically (or chemically) between different color states. A family of redox-active copolymers is described in U.S. Pat. No. 5,883,220. Another family of nitrogen based heterocyclic organic EC materials is described in U.S. Pat. No. 6,197,923. Research into still other types of organic film EC materials continues, in hopes of identifying or developing EC materials that will be useful in EC windows. There still exists room for improvement and development of new types of EC organic polymer films, and methods of making EC organic polymer films. For example, it would be desirable to develop EC organic polymer films and methods for making such materials that provide certain desirable properties, such as specific colors, long-term stability, rapid redox switching, and large changes in opacity with changes of state.

SUMMARY

Disclosed herein are several concepts related to green EC polymer materials. A first aspect of the concepts disclosed herein is an EC device including a green EC polymer, which exhibits its green color due to the presence of a single absorption band.

There are two basic reasons why a material will exhibit a green color. The first reason is based on the principle of complementary colors. Three pairs of complementary colors are red/green, blue/orange, and yellow/purple. If a material absorbs red light (with a wavelength of approximately 620 nm to 780 nm) from white light, the material exhibits a green color. The disclosure provided herein encompasses several different materials exhibiting a single absorption peak between 620 nm and 780 nm (i.e., materials which are green because their single absorption band absorbs red light, the complementary color for green). A second reason why a material will exhibit a green color is if the material includes two different absorption bands, a first absorption band that absorbs light with a wavelength less than about 480 nm (i.e., violet and blue light), and a second absorption band that absorbs light with a wavelength above about 530 nm (i.e., yellow, orange, and red light). Only green light will be left after this subtraction of the other colors, and such materials will exhibit a green color. The disclosure provided herein encompasses several different materials exhibiting dual absorption peaks, which absorb all colors but green.

A second aspect of the concepts disclosed herein is a heretofore unknown synthesis for 2,5-di(thien-2-yl)-3,4-di(2,2,2-trifluoro-ethoxy)-thiophene, a green EC monomer based on thiophene. A detailed description of the synthesis of 2,5-di (thien-2-yl)-3,4-di(2,2,2-trifluoro-ethoxy)-thiophene is provided below.

A third aspect of the concepts disclosed herein is a method for polymerizing 2,5-di(thien-2-yl)-3,4-di(2,2,2-trifluoro-ethoxy)-thiophene, using either cyclic voltammetry or a combination of chronoamperometry and cyclic voltammetry. A detailed description of the polymerization of 2,5-di(thien-2-yl)-3,4-di(2,2,2-trifluoro-ethoxy)-thiophene is provided below.

A fourth aspect of the concepts disclosed herein is a modification of the synthesis for 2,5-di(thien-2-yl)-3,4-di(2,2,2-trifluoro-ethoxy)-thiophene, enabling the 2,2,2-trifluoro functional group to be replaced with a different fluorine containing functional group. A detailed description of this alternative synthesis is provided below.

A fifth aspect of the concepts disclosed herein is a heretofore unknown synthesis for yet another thiophene derivative, 2,5-(2,3-dihydro-thieno[3,4-b][1,4]dioxin-yl)-3,4-di(2,2,2-trifluoro-ethoxy)-thiophene. A detailed description of the synthesis of 2,5-(2,3-dihydro-thieno[3,4-b][1,4]dioxin-5-yl)-3,4-di(2,2,2-trifluoro-ethoxy)-thiophene is also provided below.

A sixth aspect of the concepts disclosed herein is a modification of the synthesis for 2,5-(2,3-dihydro-thieno[3,4-b][1,4]-dioxin-5-yl)-3,4-di-(2,2,2-trifluoro-ethoxy)-thiophene, enabling the 2,2,2-trifluoro functional group to be replaced with a different fluorine-containing functional group. A detailed description of this alternative synthesis is provided below.

A seventh aspect of the concepts disclosed herein is a method for polymerizing 2,5-(2,3-dihydro-thieno[3,4-b][1,4]-dioxin-5-yl)-3,4-di-(2,2,2-trifluoro-ethoxy)-thiophene, using cyclic voltammetry. A detailed description of this polymerization is provided below.

An eighth aspect of the concepts disclosed herein is a heretofore unknown synthesis for a green EC material, which exhibits a green color due to two absorption peaks, and is a pyrazine derivative, 2,3-dibenzyl-5,7-di(thien-2-yl)thieno[3,4-b]pyrazine. A detailed description of the synthesis 2,3-dibenzyl-5,7-di(thien-2-yl)thieno[3,4-b]pyrazine is provided below.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A graphically illustrates a typical absorption spectrum of a green material exhibiting a single absorption peak;

FIG. 1B graphically illustrates a typical absorption spectrum of a green material exhibiting dual absorption peaks;

FIG. 2 illustrates the structure of a thiophene derivative that exhibits a slight yellow color in its neutral state, and which exhibits a dark green color in a charged state;

FIG. 3 schematically illustrates the synthesis of the thiophene derivative, the structure of which is shown in FIG. 2;

FIGS. 4A and 4B schematically illustrate an empirical EC device that includes the thiophene derivative, the structure of which is shown in FIG. 2;

FIGS. 5A and 5B schematically illustrate another empirical EC device that includes the thiophene derivative, the structure of which is shown in FIG. 2;

FIG. 5C graphically illustrates transmittance data for the EC polymer device of FIGS. 5A and 5B, in both the oxidized and reduced states;

FIG. 6 illustrates the structure of a charge-balancing molecule incorporated into the EC device of FIGS. 5A and 5B;

Figure 7A:
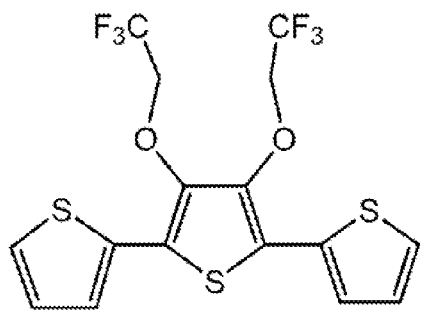
FIGS. 7A-7F illustrate the structure of materials investigated to identify candidates for a single band green EC polymer.
Figure 7B:
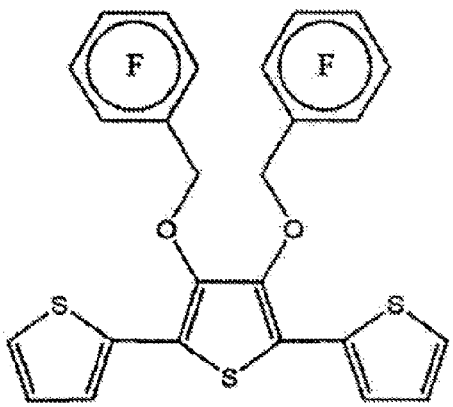
Figure 7C:
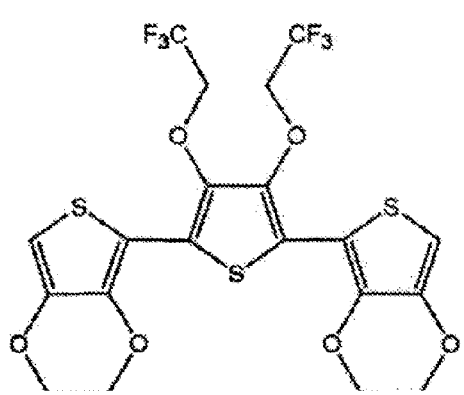
Figure 9:
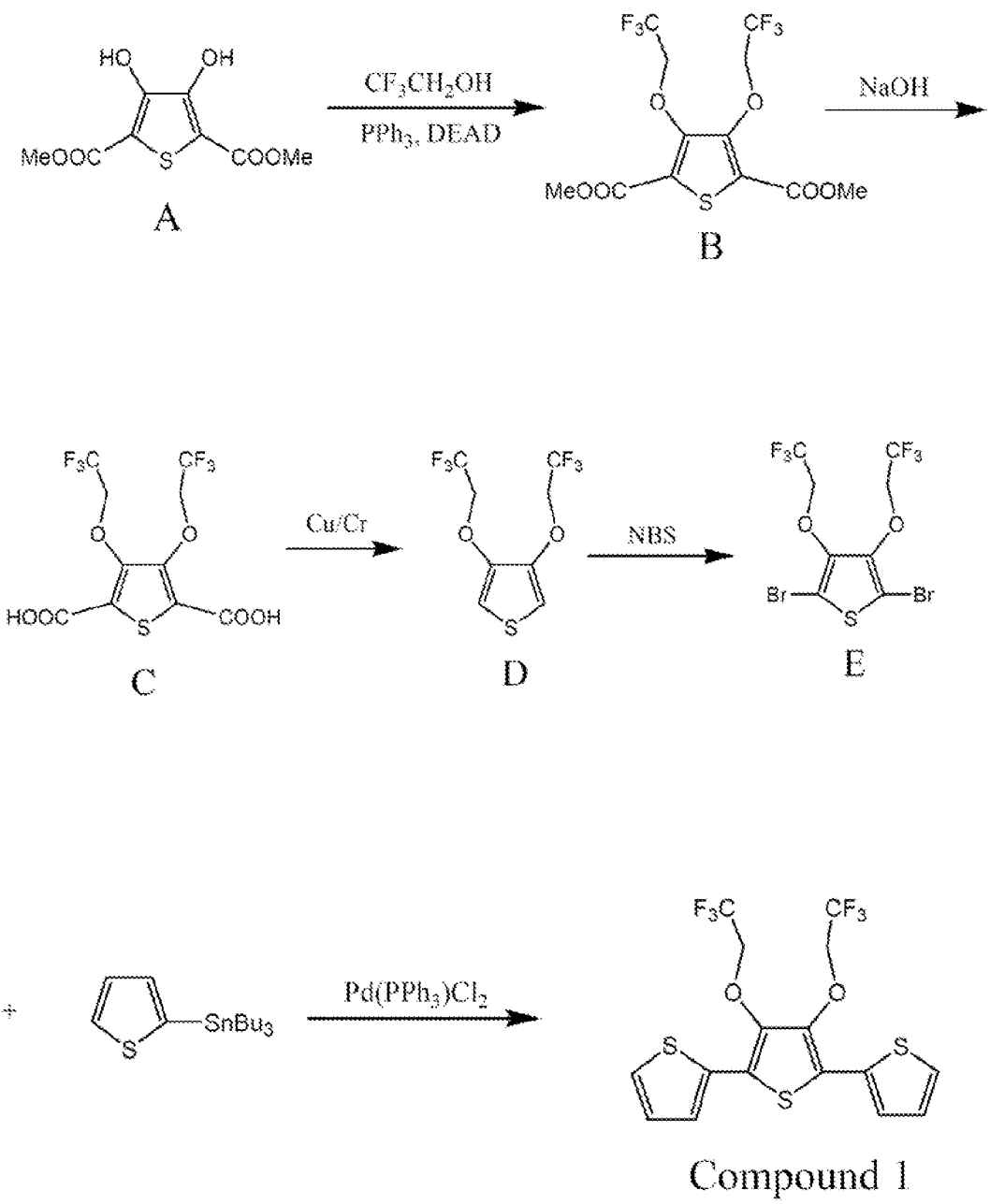
Figure 11A:
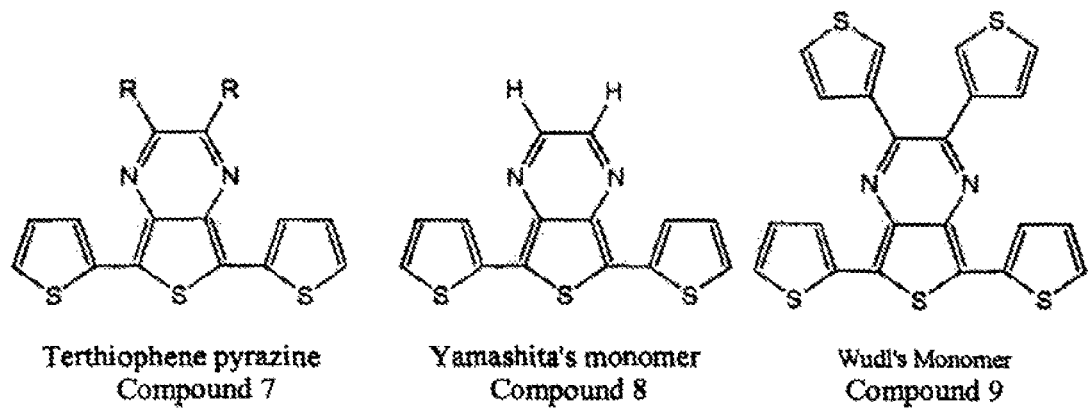
Figure 11B:
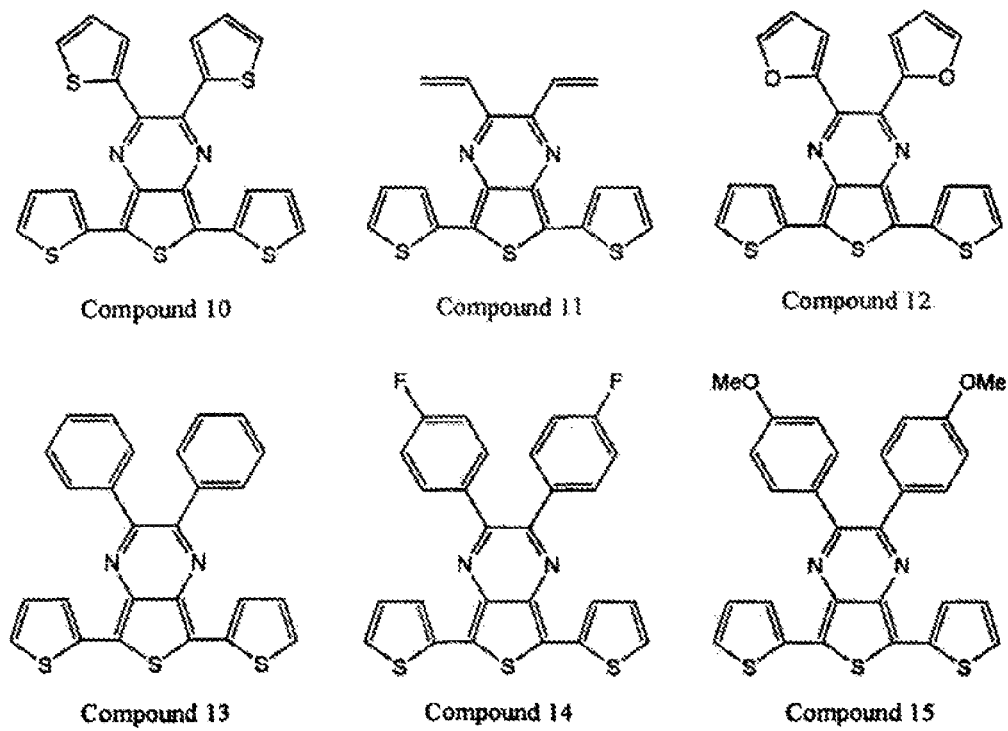
Figure 15:
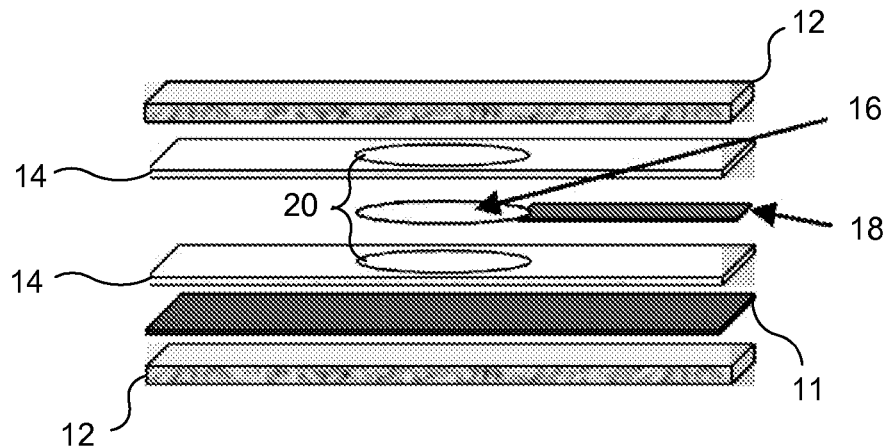
Figure 16A:
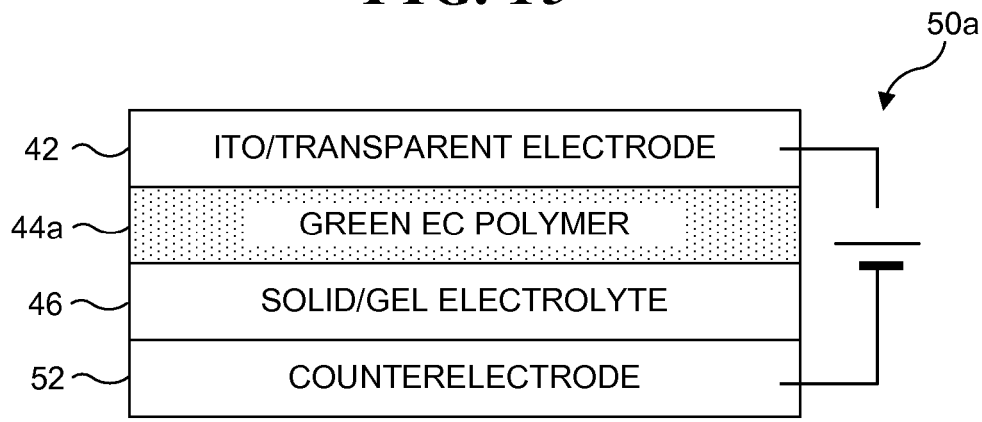
Figure 16B:
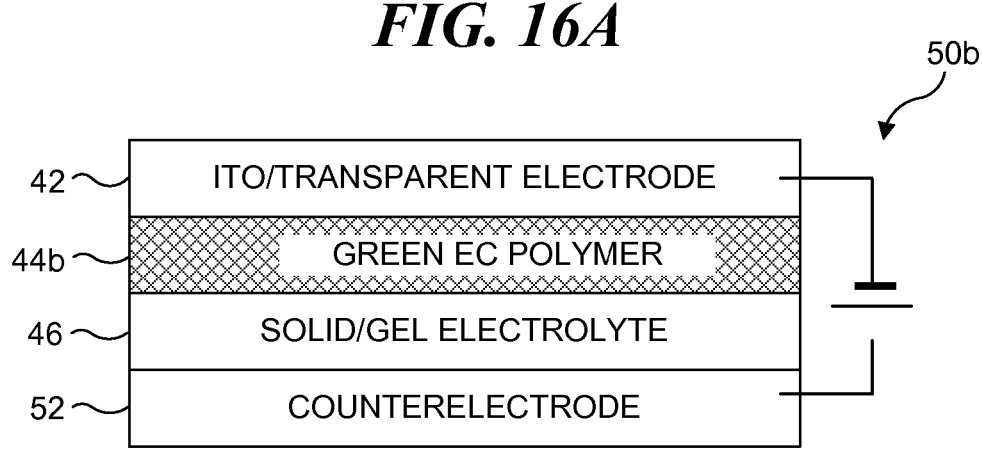

FIG. 8 graphically illustrates transmittance data for Compound 1 of FIG. 7A, in its oxidized and reduced states;

FIG. 9 schematically illustrates the synthesis of Compound 1 of FIG. 7A, which may be beneficially employed as a green EC polymer, once it has been polymerized;

FIG. 10A schematically illustrates the synthesis of Compound 3 of FIG. 7C, which may potentially be employed as a green EC polymer, once it has been polymerized;

FIG. 10B graphically illustrates transmittance data for Compound 3 of FIG. 7C, in both its oxidized and reduced states;

FIG. 11A (Prior Art) illustrates the structure of known materials exhibiting a green color based on dual absorption bands, which served as a basis for investigating new materials to identify candidates for a dual-band green EC polymer;

FIG. 11B illustrates the structure of six newly synthesized compounds developed while attempting to produce a dual-band green EC polymer;

FIG. 12 schematically illustrates the synthesis of Compound 13 of FIG. 11B, which may potentially be employed as a green EC polymer, once it has been polymerized;

FIG. 13 is a flowchart showing exemplary logical steps executed in a first electropolymerization technique for producing EC polymer films from monomers;

FIG. 14 is a flowchart illustrating exemplary logical steps executed in a second electropolymerization technique for producing EC polymer films from monomers;

FIG. 15 schematically illustrates an exemplary EC device including a green EC polymer; and FIGS. 16A and 16B schematically illustrate another exemplary EC device including a green EC polymer.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Particularly with respect to the synthesis methods disclosed herein, it should be noted that the times indicated in the methods disclosed are intended to be exemplary, rather than limiting. For exampling, a step of refluxing a solution for 30 minutes can be considered to be refluxing for a relatively shorter period of time, while a step of refluxing a solution for 17 hours can be considered to be refluxing for a relatively longer time (or refluxing for an extended period). It should be recognized that the concepts disclosed herein encompass longer and shorter times than those provided as exemplary times. Similarly, quantities of reagents are also intended to be exemplary. Further, where a particular solvent, catalyst or other reagent is named, it must be recognized that equivalent reagents (i.e., similar solvents, catalysts or reagents) can often be substituted without substantially effecting the product being synthesized.

Exemplary embodiments are illustrated in referenced Figures of the drawings. It is intended that the embodiments and Figures disclosed herein are to be considered illustrative rather than restrictive.

Figure 1A:
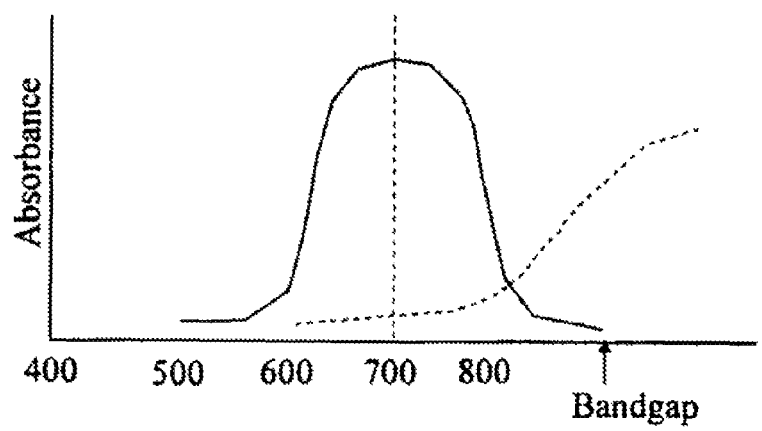
Figure 1B:
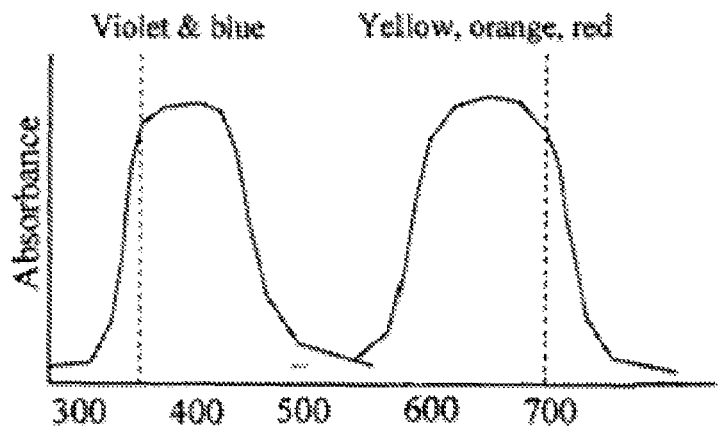

As noted above, materials exhibiting a green color can either exhibit a single absorption peak between about 620 nm and about 780 nm, or instead, exhibit two different absorption bands, a first absorption band that absorbs light with a wavelength less than about 480 nm (i.e., violet and blue light), and a second absorption band that absorbs all light with a wavelength above about 530 nm (i.e., yellow, orange, and red light). FIG. 1A graphically illustrates a typical absorption spectrum of green material exhibiting a single absorption peak, while FIG. 1B graphically illustrates a typical absorption spectrum of green material exhibiting dual absorption peaks.

First Exemplary Green EC Material Exhibiting a Single Absorption Peak

Figure 2:
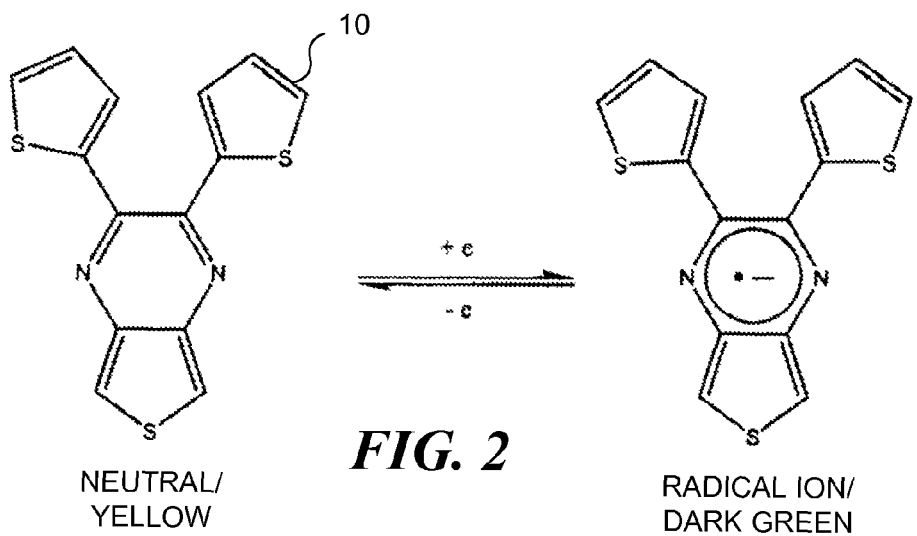

A first exemplary green material exhibiting a single absorption peak that can be used as a green EC polymer is a thiophene derivative, 2,3-di-thiophen-2-yl-thieno[3,4-b]pyrazine, which originally was evaluated for use as a nonlinear optical material. FIG. 2 illustrates the chemical structure of a thiophene derivative 10 in both a neutral state and in a charged state. In the neutral state, thiophene derivative 10 exhibits a very slight yellow color. Thiophene derivative 10 can be reduced to a radical ion, which has an absorption peak at about 680 nm and exhibits a very saturated green color. The transition from the radical ion (dark green) to the neutral state (pale yellow) is reversible, indicating that thiophene derivative 10 can be used as a green EC material.

FIG. 3 schematically illustrates the synthesis of the thiophene derivative of FIG. 2. This synthesis route was developed while conducting research regarding the potential of the thiophene derivative for use as a nonlinear optical material. Significantly, this research did not involve investigating the use of thiophene derivative 10 as an EC material. As indicated in FIG. 3, thiophene is treated with NBS to yield 2,5-dibromothiophene, which is then treated with a mixture of nitric and sulfuric acids. The resulting 2,5-dibromo-3,4-dinitro-thiophene is treated with tin and HCl to yield 3,4-diamino-thiophene. The diamino-thiophene is combined with 1,2-di-thiophen-2-yl-ethane-1,2-dione in the presence of heat to yield 2,3-di-thiophen-2-yl-thieno[3,4-b]pyrazine.

Empirical EC Devices Incorporating 2,3-di-thiophen-2-yl-thieno[3l4-b]pyrazine

A first empirical electrochromic device was fabricated and includes two indium tin oxide (ITO) glass slides (functioning as transparent electrodes), a silver foil reference electrode, thiophene derivative 10, an electrolyte (tetrabutylammonium hexafluorophosphate), and a non-aqueous solvent (either acetonitrile or propylene carbonate). The completed device is readily switched between a saturated green state and a generally transparent light yellow state by a power source ranging from about −2 volts to about 0 volts. This empirical study verified that thiophene derivative 10 can be used to fabricate an EC device in which a color change of the device is from substantially transparent to a saturated green. This device is shown in FIGS. 4A and 4B. Note that thiophene derivative 10 is dissolved in a liquid electrolyte in this example.

A second empirical EC device was constructed to further study thiophene derivative 10 as a green EC material. The second empirical EC device did not incorporate a reference electrode. Instead, a charge balancing molecule, 5,10-dihydro-5,10,dimethylphenazine, was added to reduce the operation potential of the second empirical EC device. The second empirical EC device was switched between states by a potential difference as low as 1.2 volts. The switching speed between states was as fast as 0.4 seconds. Fabrication of the second empirical EC device was simple, because the reference electrode of the first empirical EC device was eliminated. Preliminary results showed that the second empirical EC device has a long cycle life, easy operation, and provides a vibrant color. The second empirical device is schematically illustrated in FIGS. 5A and 5B. FIG. 5C graphically illustrates transmittance data for the EC polymer device of FIGS. 5A and 5B in the oxidized and reduced states.

Note that, as indicated above, a charge balancing molecule is incorporated into the electrolyte layer of the second empirical EC device to reduce the switching potential. FIG. 6 schematically illustrates the structure of the charge balancing molecule, and its redox mechanism, which facilitates charge balancing.

Design Considerations for One-Band Green EC Materials

In order to achieve a conducting polymer that absorbs red light (preferably exhibiting a maximum absorption around 750 nm), the conducting polymer must have a band gap at about 1 electron volt or lower. Such conducting polymers include low band gap polymers (also known as "small band gap," or "narrow band gap" polymers). Several strategies can be implemented to synthesize low band gap polymers, including alternating the length of the conjugated structure, and introducing electron donating and withdrawing groups into the structure. A plurality of green EC materials have been developed using the above-identified synthesis strategies. Several materials were identified, which exhibited a green color in one state, and a different substantially nontransparent color in a second state. Such materials are less desirable than EC materials that exhibit a green color in a first state and a substantially transparent color in a second state. Other materials were synthesized as monomers, but proved difficult to polymerize. Several materials did exhibit the desired color transition (i.e., from a generally transparent state to a green state) and were successfully polymerized.

FIGS. 7A-7F schematically illustrate the structure of materials investigated to identify candidates for a single band green EC polymer. Compound 1, whose structure is provided in FIG. 7A, was successfully polymerized, and exhibited a color change from red to green (although the non-green color state is red and not substantially transparent, an EC polymer switching between red and green color state will be potentially useful, because some displays function by switching pixels between red, blue, and green states). Empirical testing indicates that the monomer is stable, and the colors exhibited by the polymer are aesthetically acceptable.

Compound 2, whose structure is provided in FIG. 7B, exhibited the desirable color change of substantially colorless to green; however, Compound 2 was not successfully polymerized.

Compound 3, whose structure is provided in FIG. 7C, was successfully polymerized, and exhibited a color change from purple to green.

Figure 7D:
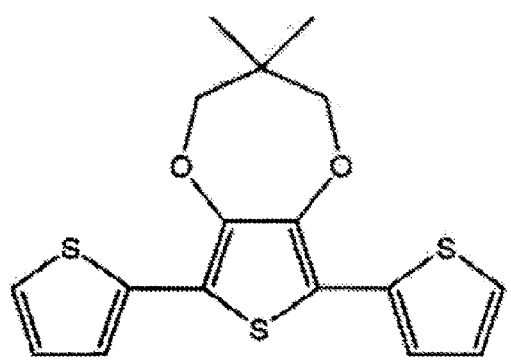

Compound 4, whose structure is provided in FIG. 7D, was successfully polymerized, and exhibited a color change from orange to dark green.

Figure 7E:
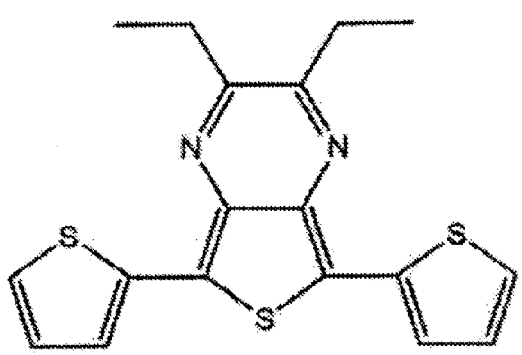

Compound 5, whose structure is provided in FIG. 7E, was successfully polymerized, and exhibited a color change from substantially opaque (i.e., dark) to green.

Figure 7F:
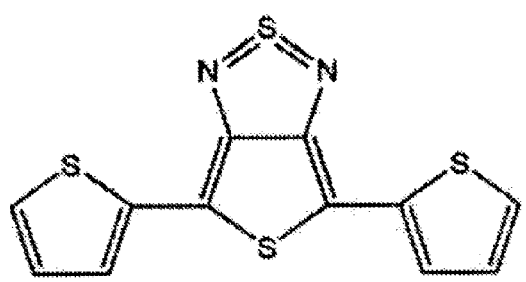

Compound 6, whose structure is provided in FIG. 7F, was successfully polymerized, and exhibited a color change from dark gray to green. Testing determined that Compound 6 is not electrochemically stable.

Based on the results of the study noted above, it was determined that Compound 1 and Compound 3 warranted further evaluation. FIG. 8 graphically illustrates transmittance data for Compound 1, the structure of which is shown in FIG. 7A, in both the oxidized and reduced states.

Exemplary Synthesis for Compound 1 (FIG. 7A)

FIG. 9 schematically illustrates the synthesis of Compound 1 (i.e., 2,5-di(thien-2-yl)-3,4-di(2,2,2-trifluoro-ethoxy)-thiophene), the structure of which is shown in FIG. 7A, which may be beneficially employed as a green EC polymer once it has been polymerized.

Synthesis of Compound B: In the following discussion, Compound A is 3,4-dihydroxy-thiophene-2,5-dicarboxylic acid dimethyl ester; and Compound B is 3,4-bis-(2,2,2-trifluoro-ethoxy)-thiophene-2,5-dicarboxylic acid dimethyl ester.

In this method, 3,4-dihydroxy-thiophene-2,5-dicarboxylic acid dimethyl ester, the thiophene derivative labeled A in FIG. 9 (hereinafter referred to as Compound A) is first synthesized from commercially available chemicals according to prior art techniques (see K. Zong, L. Madrigal, L. B. Groenendaal, R. Reynolds, *Chem. Comm.*, 2498, 2002). Then, a solution of Compound A, 2,2,2-trifluoroethanol, $PPh_3$, and DEAD is refluxed in THF for about 15-24 hours (preferably under an inert atmosphere). The reaction mixture is evaporated to dryness. The resulting material is loaded into a silica gel column and eluded by hexane and dichloromethane (4:1, 2:1, 1:1, volume ratio) to yield 3,4-bis-(2,2,2-trifluoro-ethoxy)-thiophene-2,5-dicarboxylic acid dimethyl ester, the thiophene derivative labeled B in FIG. 5 (hereinafter referred to as "Compound B").

A yield of 25% for Compound B was obtained using the following reaction parameters: 3.00 g, (12.92 mmol) of Compound A; 2.84 g (2.2 eq) of 2,2,2-trifluoroethanol; 7.46 g (2.2 eq) of $PPh_3$; 5.00 ml (2.45 eq) of DEAD; and 45 ml of THF. An Argon reflux for 21 hours generated 1.30 g of Compound C (a white solid), which is equal to a product yield of about 25%.

Synthesis of Compound C: In this discussion, Compound C is 3,4-bis-(2,2,2-trifluoro-ethoxy)-thiophene-2,5-dicarboxylic acid.

Next, a quantity of Compound B is dissolved in a solution of sodium hydroxide and ethanol and stirred for about 12-20 hours (preferably under an inert atmosphere) while maintaining a constant temperature of about 50-70° C. The resulting solution is cooled, and any excess sodium hydroxide is neutralized using concentrated hydrochloric acid (not specifically identified in FIG. 9). The reaction product is collected using an ether extraction and purified by loading the product into a silica gel column and eluding using hexane and ethyl acetate (1:1, 1:2, volume ratio). This procedure yields 3,4-bis-(2,2,2-trifluoro-ethoxy)-thiophene-2,5-dicarboxylic acid, the thiophene derivative labeled C in FIG. 9 (hereinafter referred to as Compound C).

A yield of about 51% for Compound C was obtained using the following reaction parameters: 1.30 g (3.28 mmol) of Compound B was dissolved in a solution of 1.30 g (32.5 mmol) of sodium hydroxide, and 45 ml of ethanol, and stirred at 60° C. under Argon for 16 hours. Excess sodium hydroxide was neutralized using 3 ml of concentrated HCl. The product was collected using the ether extraction and elution techniques noted above, yielding about 0.62 g of Compound C, which is equal to a product yield of about 51%.

Synthesis of Compound D: In the following discussion, Compound D is 3,4-bis-(2,2,2-trifluoro-ethoxy)-thiophene.

A quantity of Compound C is dissolved in quinoline and a barium promoted copper chromite catalyst is added. Those of ordinary skill in the art will recognize that "barium promoted" refers to the incorporation of small amounts of barium in a catalyst, to increase the performance of the catalyst. Barium promoted copper chromite catalyst is available from Strem Chemicals, Inc. of Newburyport, Mass. The chemical formula of the barium promoted copper chromite catalyst is as follows: 62-64% $Cr_2CuO_4$, 22-24% CuO, 6% BaO, 0-4% Graphite, 1% $CrO_3$, and 1% $Cr_2O_3$. The solution of quinoline and the barium promoted copper chromite catalyst is labeled Cu/Cr in FIG. 9 (hereinafter referred to as solution Cu/Cr). The solution of Compound C and solution Cu/Cr is heated to about 170-190° C. for about 12-18 hours (preferably under an inert atmosphere). The reaction mixture is cooled, and then, the reaction product is extracted using an ether workup (those of ordinary skill in the art will recognize that such an ether workup is a common technique in organic chemical synthesis and need not be described in greater detail). The extracted reaction product is dried over magnesium sulfate and purified using a silica gel column and elution with hexane and dichloromethane (1:1, volume ratio), yielding the fluorinated EC monomer 3,4-bis-(2,2,2-trifluoro-ethoxy)-thiophene (labeled D in FIG. 9 and corresponding to Compound D as used herein), a white solid.

A yield of 42% for the fluorinated EC monomer 3,4-bis-(2,2,2-trifluoro-ethoxy)-thiophene (Compound D) was obtained using the following reaction parameters: 0.62 g (1.68 mmol) of Compound C was dissolved in 3.5 ml of quinoline, with 0.15 g of barium promoted copper chromite catalyst, and heated to 150° C. for 15 hours under an Argon (inert) atmosphere. The reaction mixture was cooled, and the product was collected using the ether extraction and elution techniques noted above, yielding 0.200 g of Compound D, which is equal to a product yield of about 42%.

Synthesis of Compound E: In the following discussion, Compound E is 2,5-dibromo-3,4-bis-(2,2,2-trifluoro-ethoxy)-thiophene.

A quantity of Compound D is dissolved in a mixture of chloroform, acetic acid, and NBS (N-bromosuccinimide), and the resulting mixture is stirred at room temperature for a period of time (about 2-5 hours). The solution of Compound D is heated to boiling for about 15-45 minutes (preferably under an inert atmosphere). The reaction mixture is cooled, and then, the reaction product is extracted using an aqueous workup (those of ordinary skill in the art will recognize that such an aqueous workup is a common technique in organic chemical synthesis and need not be described herein in greater detail). The extracted reaction product is dried over magnesium sulfate and purified using a silica gel column and elution with hexane and ethyl acetate (5:1, volume ratio), yielding 2,5-dibromo-3,4-bis-(2,2,2-trifluoro-ethoxy)-thiophene (labeled E in FIG. 9, hereafter referred to as Compound E), a white crystalline solid.

A yield of about 54% for Compound E was obtained using the following reaction parameters: A solution of Compound D (1.48 g, 5.28 mmol) and NBS (2.35 g, 11.62 mmol) in chloroform (70 ml)/acetic acid (70 ml) was stirred at room temperature for three hours. Then, the mixture was refluxed under Argon (inert) for 30 minutes. After cooling, the reaction mixture was filtered with an aqueous workup. The solution was dried over magnesium sulfate. Chromatography was performed using a silica gel column with hexane/ethyl acetate (5:1 volume ratio) as solvent. About 1.26 g of white crystal was obtained, which is equal to a product yield of about 54%.

Synthesis of Compound 1: In the following discussion, Compound 1 is 2,5-di(thien-2-yl)-3,4-di(2,2,2-trifluoro-ethoxy)-thiophene.

A final synthesis step for producing Compound 1 involves refluxing a mixture of Compound E, 2-tributyltin thiophene, and dichlorobis(triphenylphosphine) Palladium (II) in tetrahydrofuran until the reaction is complete, as indicted by monitoring the reaction mixture using a technique such as Thin Layer Chromatography (TLC). The reaction mixture is loaded directly into a silica gel column and eluded using hexane/ethyl:acetate (4:1 volume ratio) as solvents, yielding quantitative amounts of a slightly yellow crystal, Compound 1 (i.e., 2,5-di(thien-2-yl)-3,4-di(2,2,2-trifluoro-ethoxy)-thiophene).

Compound 1 was obtained using the following reaction parameters: a solution of Compound E (0.300 g, 0.685 mmol), 2-tributyltin thiophene (0.562 g, 1.51 mmol), and dichlorobis(triphenylphosphine) Palladium (II) (0.5 mol %) in tetrahydrofuran (15 mL) was refluxed under Argon (inert). The reaction was monitored by TLC and was finished after 15 hours. The reaction mixture was loaded on a silica gel column directly using hexane/ethyl acetate (4:1 volume ratio) as a solvent. About 0.30 g of slightly yellow crystal was obtained. The yield was quantitative.

It should be noted that the synthesis shown in FIG. 9 can be easily modified to achieve other fluorinated EC monomers simply by replacing 2,2,2-trifluoroethanol (used to convert Compound A to Compound B) with appropriate other fluorinated alcohols, such as 2-fluoroethanol, 2,3,4,5,6-pentfluorobenzyl alcohol, and 2,2-difluoro-1,3-propanediol. Using the synthesis shown in FIG. 9, other fluorine containing EC monomers can be produced.

Starting from the production of Compound E, an alternative synthesis is as follows. A solution of Compound D (FW 280.19, 1.48 g, 5.28 mmol) and NBS (FW177.99, 2.35 g, 2.5 eq) in chloroform (70 ml) and acetic acid (70 ml) was stirred at room temperature for 16 hours. The solution was then refluxed for 30 minutes. The reaction mixture was poured into water and extracted using methylene chloride. The resulting reaction product (Compound E) was dried over magnesium sulfate and purified using chromatography purification. 1.26 g of white crystal was obtained. The yield was 54%.

Next, a solution of Compound E (FW 437.98, 0.300 g, 0.685 mmol), 2-tributyltinthiopene (FW 373.18, 0.562 g, 2.2 eq), and palladium chloride (FW 701.89, 5 mg, 0.5 mol %) in tetrahydrofuran (15 ml) was refluxed under Argon for 15 hours. The reaction mixture was dried and loaded on a column and purified with hexane and ethyl:acetate (4:1). 0.30 g of a slightly yellow crystal product was obtained. The yield was nearly 100%.

Exemplary Synthesis of Compound 3 (FIG. 7C)

FIG. 10A schematically illustrates the synthesis of Compound 3, the structure of which is illustrated in FIG. 7C, which may potentially be employed as a green EC polymer.

Synthesis of Compound 3: In the following discussion, Compound 3 is 2,5-(2,3-dihydro-thieno[3,4-b][1,4]dioxin-5-yl)-3,4-di(2,2,2-trifluoro-ethoxy)-thiophene.

Compound E is first synthesized as described above in connection with FIG. 9. A solution of Compound E, 2-tributyltin-3,4-ethylenedioxyl thiophene, dichlorobis(triphenylphosphine) Palladium (II) is refluxed in THF under an inert atmosphere for about 14-20 hours. The reaction mixture is loaded into a silica gel column and eluded by hexane/ethyl acetate (10:1, 7:1, 4:1), yielding a colorless oil (i.e., Compound 3, 2,5-(2,3-dihydro-thieno[3,4-b][1,4]dioxin-5-yl)-3,4-di(2,2,2-trifluoro-ethoxy)-thiophene).

A yield of about 27% for Compound 3 was obtained using the following reaction parameters. A solution of Compound E (0.300 g, 0.685 mmol) and 2-tributyltin-3,4-ethylenedioxyl thiophene (0.650 g, 1.51 mmol), dichlorobis(triphenylphosphine) Palladium (II) (0.5 mol %) in THF (15 mL) was refluxed under Argon (inert) for 17 hours. The reaction mixture was loaded on a silica gel column and eluded by hexane/ethyl acetate (10:1, 7:1, 4:1). 0.103 g of colorless oil was obtained. The yield was about 27%.

FIG. 10B is a UV-Vis spectra of Compound 3 in a 0.1 M LiClO$_4$ solution of acetonitrile.

An alternative synthesis is as follows. Compound E is first synthesized as described above in connection with FIG. 9. A solution of Compound E, (FW 437.98, 0.300 g, 0.685 mmol), tributyltin-(2,3-dihydro-thieno[3,4][1,4]dioxin-5-yl) (FW 431,22, 0.650 g, 2.2 eq), and palladium chloride (FW 701.89, 5 mg, 0.5 mol %) in tetrahydrofuran (15 ml) was refluxed under argon for 17 hours. The reaction mixture was evaporated and loaded onto a column. Hexane and ethyl acetate (10:1, 7:1, 4:1) were used for purification. Again, 0.103 g of colorless oil was obtained.

It should be noted that the synthesis shown in FIG. 10A can be easily modified to achieve other fluorinated EC monomers, simply by using replacing 2,2,2-trifluoroethanol (used to convert Compound A to Compound B; see FIG. 9) with appropriate other fluorinated alcohols, such as 2-fluoroethanol, 2,3,4,5,6-pentfluorobenzyl alcohol, and 2,2-difluoro-1,3-propanediol. This modification will result in a different Compound E, the starting material for the synthesis in FIG. 10A. Thus, the starting material would be: 2,5-dibromo-3,4-bis-(RO)-thiophene (i.e., a fluorinated derivative of 2,5-dibromo-3,4-dihydroxy-thiophene) rather than 2,5-dibromo-3,4-bis-(2,2,2-trifluoro-ethoxy)-thiophene, where R—OH is the fluorinated alcohol replacing 2,2,2-trifluoroethanol.

Design Considerations for Dual-Band Green EC Materials

To investigate conducting organic materials exhibiting a green color that include dual absorption bands, green monomers belonging to the terthiophene pyrazine category were investigated. FIG. 11A illustrates the structures of three known compounds from this category, respectively labeled Compound 7, Compound 8, and Compound 9.

FIG. 11B illustrates the structures of six derivatives that were synthesized based on the compounds of FIG. 11A, respectively labeled Compounds 10-15. Empirical studies indicated that Compounds 13 and 14 exhibit saturated green colors in the reduced states and are substantially transparent in the oxidized state. Based on the studies noted above, it was determined that Compound 13 warranted further study.

Exemplary Synthesis of Compound 13 (FIG. 11B)

FIG. 12 schematically illustrates the synthesis of Compound 13 of FIG. 11B, which may potentially be employed as a green EC polymer once it has been polymerized.

Synthesis of Compound 13: In the following discussion, Compound 13 is: 2,3-dibenzyl-5,7-di(thien-2-yl)thieno[3,4-b]pyrazine.

In this synthesis, 2,5-dibromo-3,4-dinitro-thiophene (Compound A) and 2-tributyltim-thiophene are combined in the presence of a palladium catalyst (such as dichlorobis (triphenylphosphine) Palladium (II)), to obtain 2,5-di(thien-2-yl)-3,4-dinitro-thiophene (Compound B).

In the presence of tin and hydrochloric acid, Compound B is converted to 2,5-di(thien-2-yl)-3,4-diamino-thiophene (Compound C).

Then, a solution of Compound C (0.300 g, 1.08 mmol), benzil (0.227 g, 1.08 mmol), and p-toluene sulfonate acid (9 mg, 5 mol %) in chloroform (20 mL) was refluxed under Argon (inert) for 17 hours. The reaction mixture was evaporated and the residue was loaded into a silica gel column. Methylene chloride/hexane (1:1) was used to elude the compound. About 0.350 g of purple solid was obtained. The yield was thus about 72%.

Exemplary Polymerization Techniques

One aspect of the present disclosure is directed to a method for producing EC polymer films using electropolymerization. Two related electropolymerization techniques can be employed to polymerize EC monomers in order to achieve a high quality EC polymer film. Density is required to achieve the high contrast between the bleached and unbleached states. High quality is required for repeatability over many cycles. EC polymer films that do not exhibit high contrast and repeatability over many cycles are not very useful as components in EC polymer-based devices, such as windows and displays.

EC polymer films were produced based on Compound 1, Compound 3, and Compound 13. Specific parameters of these polymerizations are described below. An overview of the two basic electropolymerization techniques is described as follows.

A first electropolymerization technique is summarized in a flow chart 200 in FIG. 13. EC monomers are prepared in a block 202, and then cyclic voltammetry is employed, as indicated in a block 204, to polymerize the EC monomer and to deposit the resultant polymer as a film on a substrate, preferably an indium tin oxide (ITO) coated transparent substrate.

The second electropolymerization technique in accord with the present invention is summarized in a flow chart 212 in FIG. 14. Once again, EC monomers are prepared in a block 214 (as described above). Once the starting monomer is obtained or prepared, the monomer is polymerized first using chronoamperometry, as indicated in a block 216, followed by cyclic voltammetry, as indicated in a block 218. The second electropolymerization technique combining both chronoamperometry and cyclic voltammetry appears to achieve a higher quality, more durable EC polymer film.

Referring now to block 216 of FIG. 14, the first step in the two part electropolymerization of the EC monomer can be achieved using chronoamperometry under the following conditions. Oxidative electrochemical polymerization of the monomer is initiated using chronoamperometry to deposit a very thin, very uniform layer of EC polymer onto an ITO coated glass substrate using a platinum wire as a counter electrode. Once again, the selected monomer is placed into a solvent/salt solution, such as a propylene carbonate solution with tetrabutylammonium perchlorate salt.

In a block 218, multiple scan cyclic voltammetry is employed to deposit additional polymer onto the uniform layer deposited using chronoamperometry. Additional cycles may be required for the deposition of an acceptably dense layer of polymer.

Exemplary Polymerization of Compounds 1 and 3

The following technique was used to successfully achieve a stable polymer based on Compound 1. Compound 1 (22 mg) and lithium perchlorate (53 mg) are dissolved in acetonitrile (5.0 ml). The resulting solution contains 0.01 M of Compound 1 and 0.10 M of lithium perchlorate. The solution is purged by Argon for 15 minutes before electrochemical polymerization. A potentiostat and three electrode setup are used with ITO as working electrode, platinum wire as a counter electrode, and silver wire as a reference electrode. The electrodes are cleaned and dried carefully prior to use. The polymerization can be done in two ways. The first approach is by applying the cyclic voltammetry method. The parameters include a scanning range of −0.1 volts to 1.1 volts, and a scanning rate of 50 mV/s for 10 cycles. The second approach is carried out by applying chronoamperometry. The potential applied is 1.2 volts for 20 s (versus an Ag reference electrode).

The same technique can be used to polymerize Compound 3.

Exemplary Polymerization of Compound 13

The following technique was used to successfully achieve a stable polymer based on Compound 13. Compound 13 (23 mg) and tetrabutylammonium hexafluorophosphate (193 mg) are dissolved in methylene chloride (2.5 ml) and acetonitrile (2.5 ml). The resulting solution contains 0.01 M of Compound 13 and 0.10 M of tetrabutylammonium hexafluorophosphate. The solution is purged by Argon for 15 minutes before electrochemical polymerization. A potentiostat and three electrode setup are used with ITO as the working electrode, a platinum wire as a counter electrode, and a silver wire as a reference electrode. The electrodes are carefully cleaned and dried prior to use. Cyclic voltammetry is used for polymerization. The parameters include a scanning range of −0.05 to 0.85 volts (versus an Ag reference electrode), and a scanning rate of 20 mV/s for 8 cycles.

Exemplary EC Devices Including Green EC Polymers

FIG. 15 schematically illustrates an EC device including a green EC polymer, such as Compounds 1, 3, or 13, as discussed in detail above. A first layer is implemented by ITO transparent electrode 12, followed by an insulating layer 14 (which can be implemented using a non-conductive and transparent polymer such as a parafilm). A reference electrode 18 (preferably implemented using a silver electrode) is sandwiched between upper and lower insulating layers 14. A layer of a green EC polymer 11 is sandwiched between lower insulating layer 14 and a lower transparent electrode 12. Note that each insulating layer includes an opening 20, which is filled with an electrolyte 16. The openings enable electrical charges to be exchanged between the transparent electrodes, the reference electrode, the electrolyte, and the green EC polymer.

A plurality of different electrolytes can be employed. An important component of an EC device is the electrolyte, which must be ionically conductive, but electronically insulating. The use of a semi-solid (or gel) electrolyte is preferred. Such gel electrolytes generally are formed by combining an alkali metal salt (a source of ions) with a polymer host (for stability). For a gel electrolyte to be suitable for smart windows or smart displays, it is important that the gel electrolyte provide high ionic conductivity, high light transmittance (i.e., be optically clear), and be stable over a wide range of time and temperatures. High ionic conductivity is essential in an EC device, because the ions need to freely and quickly migrate within the polymer matrix. Electric conductivity should be negligible, so that the device does not short circuit. For smart window applications, a high light transmittance is also important to maximize the transparency of the window in the bleached state.

Stability is equally vital in an EC device. There should be a minimal change in conductivity and transmittance for gel electrolytes measured over time and at various temperatures. These parameters can vary, depending on the salt and solvent combinations used.

In general, gel electrolytes offer superior conductivity compared to entirely solid polymer electrolytes. While liquid electrolytes can be employed, gel electrolytes offer the advantages of mechanical stability (thus facilitating leak-free devices), low weight, and established lifetimes of at least 50,000 cycles, as empirically determined. In a gel electrolyte, the solid polymer matrix of polyvinyl chloride (PVC) and polymethylmethacrylate (PMMA) provides dimensional stability to the electrolyte, while the high permittivity of the solvents enables extensive dissociation of the lithium salts. The low viscosity of the solvents provides an ionic environment that facilitates high ionic mobility. A variety of different combinations of salts and solvents have been studied to determine optimum combinations.

Highly conductive gel electrolytes have been synthesized from a salt dissolved in an electrolyte solution with the polymer matrix, with PMMA added for dimensional stability. Lithium (Li) is commonly used as the salt in EC switching devices due to its small size and because it facilitates the reduction and oxidization of EC polymers. Another salt, tetrabutyl ammonium phosphate (TBAP), can also be employed. Overall, the salt must have a high degree of dissociation and the anion must have a high level of charge delocalization so that the ion-pairing is minimized.

An exemplary, but not limiting list of possible salts includes lithium perchlorate ($LiClO_4$), tetrabutyl ammonium perchlorate (TBAP), and trifluorosulfonimide ($LiN(CF_3SO_2)_2$). An exemplary, but not limiting list of solvents includes propylene carbonate (PC), ethylene carbonate (EtC), acetonitrile (ACN), and γ-butyrolactone (GBL). Preferably, solvents are substantially dried over molecular sieves before their use. In general, gel electrolytes are synthesized by first dissolving the salt in the solvent, and then adding the PMMA. A highly conductive (2 mS/cm), viscous and transparent (88%) gel electrolyte can generally be achieved in this manner.

Still another useful gel electrolyte can be prepared from 3% $LiClO_4$, 7% PMMA, 20% PC, and 70% acetonitrile (ACN) (% by weight). A simple synthesis of such a gel was achieved by first dissolving the PMMA and $LiClO_4$ in ACN. The PC was dried over 4 angstrom molecular sieves and then combined with the other ingredients. The complete mixture was stirred for 10-14 hours at room temperature. A high conductivity (2 mS/cm), high viscosity, and transparent gel electrolyte was thus formed. As described above, the solid polymer matrix of PMMA provides dimensional stability to the electrolyte, while the high permittivity of the solvents PC and ACN enable extensive dissociation of the lithium salt. The low viscosity of PC provides an ionic environment that facilitates high ionic mobility.

While gel electrolytes are preferred because they facilitate the production of a solid state device (the solvent liquid is contained within the polymer matrix), liquid electrolytes can be used in an EC device. One such liquid electrolyte can be achieved, for example, using 0.1 M tetrabutylammonium perchlorate (TBAP) in ACN. It is contemplated that materials other than PVC and PMMA can be employed to provide a polymer matrix for a gel electrolyte, and that materials other than TBAP and $LiClO_4$ can be employed as ionic sources. It should be noted that in the context of the present technology, the terms "gel electrolyte" and "solid electrolyte" are use synonymously, because the liquid materials employed in fabricating a gel electrolyte are absorbed in a polymer matrix, and there are substantially no free liquids that are not contained within the polymer matrix.

A second exemplary EC device including a green EC polymer is schematically illustrated in a transparent state 50a in FIG. 16A, and in a colored state 50b in FIG. 16B. From a structural standpoint, there is no difference in the EC device when in its transparent state or its colored state. The second exemplary EC device, as illustrated in both of its states in FIGS. 16A and 16B, includes a green EC polymer layer and a counter-electrode layer. Again, the top layer is transparent electrode 42, again, preferably ITO. The next layer is the green EC polymer, which in FIG. 16A is shown as a non-green layer 44a (this layer could be transparent, as with Compound 13, or red, as with Compound 1), and in FIG. 16B is shown as a colored layer 44b (in the reduced state the green EC polymers discussed above exhibit a saturated green color). Next to the EC polymer layer is a solid/gel electrolyte layer 46. The solid electrolyte layer is followed by a counter-electrode layer 52. No bottom transparent electrode layer is required or included.

Counter-electrode layer 52 is preferably gold-based, platinum-based, or highly conductive carbon-based, or vanadium pentoxide-based. A preferred highly conductive carbon is graphite. It should be understood that while graphite certainly represents a preferred highly conductive carbon, other highly conductive carbon materials can instead be beneficially employed as a conductive film applied as a coating on a transparent substrate to produce a counter-electrode. Many types of conductive carbons are available from a variety of manufacturers, such as Tokai Carbon Co. of Tokyo, Japan; and Loresco International, of Hattiesburg, Miss. Thus, the use of the term "graphite" herein should be considered to be exemplary, rather than limiting on the scope of the present technology. It is further contemplated that nickel can be beneficially employed as a conductive film on a transparent substrate, to produce a counter-electrode. The use of a counter-electrode can improve the speed of the color change between states, as well as improve the contrast ratio between the two states. The counter-electrode material should be chemically stable, provide high electrical conductivity, and should be easy to fashion into a patterned substrate. Gold, highly conductive carbons, and platinum have been identified as electrically conductive materials that can be beneficially employed for making a counter-electrode. It is contemplated that graphite will be very useful because of its low cost. Gold, while much more expensive, can be used in very thin layers, thereby minimizing the cost of a gold-based counter-electrode. Platinum, while electrically conductive, is likely to be so expensive as to preclude its use. It is further contemplated that still other conductive materials can be employed to produce the counter-electrode.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. An electrochromic device comprising:
    (a) a transparent electrode;
    (b) an electrochromic organic material that in a first state is not green and in a second state exhibits a green color, the electrochromic organic material exhibiting a single absorbance band, wherein the green electrochromic organic material exhibiting a single absorbance band comprises an electrochromic polymer based on a fluorinated derivative of 2,5-(2,3-dihydro- thieno[3,4][1,4]-dioxin-5-yl)-3,4-dihydroxy-thiophene, the fluorinated derivative corresponding to 2,5-(2,3-dihydro-thieno[3,4][1,4]-dioxin-5-yl)-3,4-di(R-oxy)-thiophene, with R corresponding to a fluorinated functional group; and
    (c) an electrolyte.

* * * * *